| United States Patent [19] | [11] Patent Number: 4,812,404 |
| Kuboki et al. | [45] Date of Patent: Mar. 14, 1989 |

[54] APATITE IMMOBILIZED GLUCANASE

[75] Inventors: Yoshinori Kuboki, Chiba; Daisaburo Fujimoto, Hamamatsu; Hideki Aoki; Keijiro Fujita, both of Tokyo, all of Japan

[73] Assignee: Dental Kagaku Kabushiki Kaisha, Tokyo, Japan

[21] Appl. No.: 878,256

[22] Filed: Jun. 25, 1986

[30] Foreign Application Priority Data

Sep. 20, 1985 [JP] Japan ................................ 60-206677

[51] Int. Cl.$^4$ ...................... C12N 11/18; C12N 11/14; C12N 9/36; C12N 9/46
[52] U.S. Cl. ................................... 435/175; 435/176; 435/206; 435/211
[58] Field of Search ............... 435/174, 175, 176, 177, 435/206, 211

[56] References Cited

U.S. PATENT DOCUMENTS 4,155,546 9/1978 Uidra et al. .................. 435/211 X
4,464,468 8/1984 Arrameas et al. ................ 435/177

OTHER PUBLICATIONS

Hasselberger, F. X., Uses of Enzymes and Immobilized Enzymes, Xlelson-Hall, Chicago, 1978, pp. 130-131.
Zaborsky, O., Immobilized Enzymes, CRC Press, Cleveland, Ohio, 1973, pp. 70-82.
The Condensed Chemical Dictionary, 8th Ed., VNR, NY, 1971, p. 73.

*Primary Examiner*—David M. Naff
*Attorney, Agent, or Firm*—Stevens, Davis, Miller & Mosher

[57] ABSTRACT

Apatite containing immobilized glucanase for decomposition of polysaccharies associated with dental carries is prepared by adding dropwise glutaraldehyde to an aqueous solution in which glucanase, protein and apatite are present in a mixed state. The protein in preferably lysozyme.

10 Claims, No Drawings

APATITE IMMOBILIZED GLUCANASE

BACKGROUND OF THE INVENTION

1. Field of the Invention

The present invention relates to apatite having glucanase immobilized therein, and to a method of immobilizing glucanase in apatite. "Glucanase" which is a general term for glucan-decomposing enzymes includes various enzymes. It is understood, however, that the term "gulcanase" used herein refers to levanase which decomposes levan, dextranase which decomposes dextran, and mutanase which decomposes mutan. Further, the term "apatite" refers to both hydroxyapatite and fluoro-apatite.

It is well-known that the occurrence of dental caries is due to dental plaque formed by way of polysaccharides such as, levan, dextran and mutan which are produced by a variety of oral bacteria. Consequently, it is believed that the polysaccharides produced by such bacteria should be removed to suppress the occurrence of dental plaque for the purpose of preventing dental caries. The present invention relates to apatite having immobilized enzymes for the decomposition of polysaccharides associated with dental caries, and to a method of preparing such apatite.

2. Description of the Prior Art

In the prior art, various methods have been developed for removing dental plaque in order to prevent dental caries. Such methods include scraping-off of dental plaque with the use of polishing agent such as zeolite, calcium carbonate, alumina and silica, using dextranase together with a stabilizer, etc. Until now, however, there has been no method of immobilizing enzyme, which are capable of decomposing polysaccharide responsible for the occurrence of dental caries such as levanase, mutanase and dextranase, with apatite, and there has been no apatite in which such enzymes are immobilized, as contemplated in the present invention.

Glucanase is an enzyme and relatively unstable. Accordingly, when glucanase is mixed with a dentifrice without being modified, its activity decreases with time and eventually vanishes. Dextranase is now used with dentifrice, and various stabilizers are produced to prevent the deactivation thereof. For instance, combinations of dextranase with aluminium oxide, carvone or l-mentol, and gelatin or peptone are proposed in the specifications of Japanese patent application Laid-Open Nos. 56-63915 and 56-110609 and Japanese patent publication No. 52-49005. Because dentifrice is designed to be used in the mouth, various restrictions are imposed including considerations concerning the influence upon the human body and the demand for a refreshing feeling after use. Because it is a matter of course that such restrictions are placed upon the stabilizers used, the selection of the stabilizers involves difficult problems. Use of other enzymes besides dextranase possess the same problems as the use of dextranase.

SUMMARY OF THE INVENTION

As a result of intensive and extensive studies made on the stabilization of glucose, it has been found that the immobilization of glucanase with apatite, which is used as a polishing agent yields glucanase which does not require a stabilizer and which exhibits activity over an extended period. The present invention provides apatite having glucanase immobilized therein and a method of preparing such apatite.

It is well-known that there is an enzyme-immobilizing method based on the fact that hydroxyapatite, active-carbon, kaolinite, terra abla and the like physically absorb enzymes for immobilization, and it is generally known that the immobilized enzymes are so stable that they show a lesser change in activity with time compared with an untreated enzyme and are convenient to handle. It has thus been long known that apatite firmly adsorbs and bonds thereto a certain type of protein. Based on the consideration that the immobilization of glucanase may lead to a reduction in activity change with time, it is presumed that, if glucanase is immobilized with apatite used as the polishing agent for dentifrice by the physical adsorption method, immobilized glucanase might be obtained easily and it might then be possible to obtain a desirable dentifrice material which combines a polishing capability with a polysaccharide-decomposing capability, and dispenses with any selection of stabilizer. As a result of studies made on such a presumption, it has been found that the adsorption and immobilization of glucanase on apatite is unfeasible due to the fact that the adsorption of glucanase to apatite is extremely limited. For this reason, further studies were made on the immobilization of glucanase by way of protein that is firmly adsorbed to and bonded to apatite and, in consequence, apatite having glucanase immobilized therein and a method of preparing the same were found.

The present invention provides apatite having glucanase immobilized therein and a method of immobilizing glucanase in apatite together with a certain type of protein that is firmly adsorbed to apatite.

Apatite is suspended in an aqueous solution or in a phosphate buffer solution having a concentration of 0.01 to 0.05 moles in which glucanase and protein showing strong adsorption to apatite and having no adverse influence upon the human body are dissolved, and a bifunctional aldehyde is then added dropwise under vigorous agitation to the resulting suspension at below room temperature. The protein used may be selected from albumin, casein, lysozyme, cytochrome C and the like. Depending upon the type of protein, there is a difference in the titer of the resulting immobilized enzyme and the bonding force with respect to apatite. As will be appreciated from the results of the elution test to be given later, however, preference is given to lysozyme, cytochrome C and the like. The glucanase used may be selected arbitrarily from levanase, dextranase and mutanase, as already mentioned. Optionally, mixtures of such enzymes may be used. The reaction involved takes place at a pH level at which no decomposition of apatite occurs, i.e., at a pH level of 5.6 or higher. However, because a higher pH has an adverse influence upon the adsorption of protein, a pH value above 9.0 is not preferred. The most preferred pH value is around 7.0.

It is desired that the particle size of the apatite used be as uniform as possible, however, apatite particles generally used as the polishing agent for a dentifrice are adequate for this particular purpose. Apatite having a particle size of 2 to 200 microns is preferred because it is easy to handle. The amount of the apatite used is 10 to 100 times as large as the amount of protein. For efficient agitation, it is desired that a larger amount of water be used with respect to the amount of the apatite used. The amount of water is adjusted in such a manner that the solid content in the reaction phase amounts from 4 to 20%. It is preferred that virtually equivalent amounts of protein and glucanase be used. A large difference in the amount of both components, in particular, use of glucanase in a smaller amount with respect to protein, should be avoided because there will be a drop in the titer of the resulting immobilized enzyme. Generally, available glutaraldehyde is preferred for the bifunctional aldehyde used. The amount of the bifunctional aldehyde used is a factor which produces the greatest influence upon the titer of the immobilized enzyme. Too small an amount of the glutaraldehyde to be added generally causes the immobilized enzyme to show a low bonding force to apatite and to suffer considerable deactivation with the passage of time. A large amount of glutaraldehyde results in a reduction in the titer of the obtained immobilized enzyme, and a further increase in the amount thereof leads to deactivation of that enzyme. Although the amount of glutaraldehyde used is slightly different depending upon the type of glucanase and protein, generally, the amount of glutaraldehyde used is 3 to 60 mg, preferably 6 to 20 mg per gram of protein used. The reaction involved is effected at a temperature not exceeding room temperature, preferably at around 5° C. While vigorous stirring is applied to a suspension in which protein, glucanase and apatite coexist, an aqueous solution of glutaraldehyde is slowly added dropwise thereto. After the dropwise addition, stirring is carried out at the same temperature for several hours to complete the reaction. After the reaction has been completed, filtration is applied. The obtained apatite is amply washed with water or the buffer solution used for removal of entrained protein and enzyme, and is then maintained at a lower temperature or freeze-dried for solidification and then kept at the room temperature.

This immobilized apatite according to the present invention may also be produced in the following manner. Apatite is added under sufficient agitation to an aqueous or buffer solution in which the protein is dissolved, whereby the protein is adsorbed to the apatite for saturation. Thereafter, the apatite which has adsorbed the protein is collected and added to water or buffer solution in which glucanase is dissolved. While the resulting solution is vigorously stirred, an aqueous solution of glutaraldehyde is slowly added dropwise thereto. The temperature and other conditions applied to this end are the same as mentioned in the foregoing.

The apatite having immobilized glucanase obtained in this manner, is stable, suffers less change with time and is easy to handle.

It has been clarified that apatite well absorbs a certain type of protein. It is also known that glutaraldehyde is used as the crosslinking agent for the immobilization of enzyme. Although the mechanism through which the immobilization of glucanase with apatite is achieved is stil unclear, it is presumed that the adsorption of protein, which is easily adsorbed by apatite, to apatite takes place simultaneously with crosslinking of protein and glucanase, thus yielding the immobilized apatite.

For a better understanding of the invention and to show how the same may be put into effect, reference will be made by a way of example to the following working example.

EXAMPLE 1

Immobilization of Levanase to Hydroxyapatite

One hundred (100) mg of lysozyme and 100 mg of levanase were dissolved in 50 ml of pure water, and 2 g of polishing agent hydroxyapatite was added to the resulting solution, followed by cooling down to 4° C. While maintaining the temperature at 4° C. and vigorously stirring, 2 ml of solution containing 28 mg of glutaraldehyde in 100 ml of water was slowly added dropwise. After the completion of dropwise addition, stirring was carried out for 2 hours while maintaining the temperature at 4° C. Subsequent centrifugation gave a solid product, which was in turn washed under agitation three times with 50 ml of pure water to obtain immobilized hydroxyapatite in an undried state. (Optionally, this product may be used as such). Freeze-drying gave 2.05 g of a powder. To 1 g of that powder, 10 ml of a potassium phosphate buffer solution having a pH value of 6.8 and a concentration of 1 mole was added. Stirring was carried out for 1 hr., and centrifugation was then applied to collect the filtrate. The same operation was repeated twice with the residue. The obtained filtrates were combined to determine the protein content by the lowry method. After water washing, the residue was dried to measure to weight thereof. In consequence, it was ascertained that 11.7 mg of protein was bonded to per gram of hydroxyapatite. Measurement of the levanase activity of the immobilized hydroxyapatite in the undried state by following method indicated that 0.47 g of levan was decomposed per gram of protein bonded to hydroxyapatite.

EXAMPLE 2

Immobilization of levanase to fluoroapatite

The same conditions as in Ex. 1 were applied, except that fluoroapatite was used in place of hydroxyapatite, to obtain 2.05 g of a freeze-dried product. Measurement of the bonded protein, effected in the same manner as in Ex. 1, indicated that 13.4 mg of protein was bonded to per gram of fluoroapatite. The results of measurement of the levanase activity of undried fluoroapatite also indicated that 0.54 g of levan was decomposed by per gram of the bonded protein.

EXAMPLE 3

Immobilization of mutanase to hydroxyapatite

The same conditions as in Ex. 1, except that mutanase was used in place of levanase, were applied to obtain an immobilized hydroxyapatite. Decomposition was effected in the same manner as in Ex. 1. As a result, it was confirmed that 15.0 mg of protein was bonded to per gram of hydroxyapatite. The mutanase activity of the product was measured by a method of measuring mutanase activity to be described later. In consequence, it was ascertained that 0.48 g of mutan was decomposed by gram of the protein bonded to hydroxyapatite.

EXAMPLE 4

Immobilization of mutanase to fluoroapatite

The same conditions as in Ex. 2, except for the fact that mutanase was used in place of levanase, was applied to obtain an immobilized fluoroapatite product. The results of analysis and measurement of the titer thereof, effected in the same manner as in Ex. 3, indicated that 17 may of protein was bonded to gram of fluoroapatite, and 0.45 g of mutan was decomposed by gram of the bonded protein.

EXAMPLE 5

Immobilization of dextranase to hydroxyapatite

Five(5) g of hydroxyapatite used as polishing agent, and 50 ml of a potassium phosphate buffer solution having a concentration of 0.05 moles and a pH value of 6.8 were added to a mixture of 50 mg of lysozyme with 50 mg of dextranase. The resulting product was cooled down to 4° C. and was vigorously stirred. While maintaining that temperature, 125 μl of a 0.2% aqueous solution of glutaraldehyde was added dropwise under agitation, followed by additional stirring for 5 hr. The reaction product was collected by filtration and was washed three times with 100 ml of the aforesaid buffer solution to obtain immobilized hydroxyapatite in undried state. Freezedrying yielded 5.07 g of powdery dextranase immobilized hydroxyapatite.

One(1) ml of the undried immobilized hydroxyapatite was centrifuged to obtain a precipitate. Two(2) ml of a potassium phosphate buffer solution having a concentration of 1 mole and a pH value of 6.8 was added to the precipitate, and the resulting solution was stirred for 3 hr for the desorption of the bonded protein, followed by centrifugation. With the resulting precipitate, the same operation was repeated. The filtrates were combined to measure the amount of the protein contained therein by the lowry method, and the precipitates were washed with water and then dried to measure the weight thereof. As a result, it was observed that 13.8 mg of protein was bonded to gram of hydroxyapatite. The results of measuring dextranase activity by a dextranase activity measuring method to be described later indicated that 0.415 g of dextran was decomposed by gram of the bonded protein.

EXAMPLE 6

Immobilization of dextranase to fluoroapatite

The same preparation method, analysis and titer measurement as in Ex. 5 were applied, except for the fact that fluoroapatite was employed in place hydroxyapatite, thereby obtaining 5.08 g of immobilized fluoroapatite in which 15.2 mg of protein was bonded to gram of fluoroapatite, and 0.43 g of dextran was decomposed per gram of the bonded protein.

The results obtained under varied conditions are set forth in Table 1. The conditions for treatment are the same as in the foregoing examples.

Measurement of the Titers of Enzymes

One(1) ml of the undried immobilized apatite obtained in each experiment was added to 10 ml of a 1% solution of the corresponding substrate. After the resulting solution had been stirred at 37° C. for 2 hr., the amount of the monomer formed therein was measured. Apart from this, the protein bonded to 1 ml of the undried immobilized apatite was determined by the aforesaid method. The titer of each immobilized enzyme was then expressed in terms of the amount of the monomer per gram of the protein bonded to each apatite.

The substrates used were dextran for dextranase, mutan for mutanase and levan for levanase. The amounts of dextranase and mutanase were determined from the glucose obtained through decomposition by the glucose oxidase method, and the amount of levanase was determined from the fructose obtained through decomposition with the use of high performance liquid chromatography (a column: sugar pack I) in the conventional manner.

Bonded Protein Elution Testing

The immobilized apatite obtained was packed in a column and washed with varied concentrations of a buffer solution to determine the concentration for elution of bonded protein. The bonding force of protein to apatite was then expressed in terms of the obtained measurement. Table 2 shows the results obtained from the hydroxyapatite which dextranase is immobilized. The eluate used was a potassium phosphate buffer solution having a concentration from 1 millimole to 1 mole and a pH value of 6.8, and the control applied was hydroxyapatite to which only dextranase was bonded. The results indicate that the preferred carrier is lysozyme.

Activity of Immobilized Enzymes with Elapsed Time

Examination was made of changes in activity with elapsed time of several samples of the immobilized apatite obtained according to the present invention. The samples used were all the undried immobilized products. The activity of each sample was measured by the aforesaid method. The results are set forth in Table 3. It was found that the obtained immobilized apatites all increased their activity from the first with the passage of time and showed the peak activity value after a certain period, following which there was a gradual drop in activity.

In accordance with the present invention, glucanase can be immobilized in apatite through a very simple operation. The immobilized apatite is easy to handle, is stable and suffers less change with time. In addition, the apatite product of the present invention combines the polishing property of apatite with an ability to decompose polysaccharides responsible for dental caries. Accordingly, use of the product as a dentifrice is preferred in view of the desire for prevention of dental caries. For these reasons, the invention is highly advantageous for maintaining good oral hygiene.

As many apparently widely different embodiments of the present invention can be made without departing from the spirit and scope thereof, it is to be understood that the invention is not limited to the specific embodiments thereof except as defined in the appended claims.

TABLE 1

| NO. | Type & Amt. of Protein | Type & Amt. of Glucanase | Type & Amt. of Apatite | Glutar-aldehyde | A | B |
|---|---|---|---|---|---|---|
| 7 | lysozyme 0.1 g | levanase 0.1 g | hydroxyapatite 2 g | 1.12 mg | 10.3 mg | 0.47 g |
| 8 | lysozyme 0.1 g | mutanase 0.1 g | fluoroapatite 2 g | 1.12 mg | 14.7 mg | 0.47 g |
| 9 | lysozyme 0.1 g | levanase 0.1 g | hydroxyapatite 2 g | 0.56 mg | 9.7 mg | 0.42 g |
| 10 | casein 0.1 g | levanase 0.1 g | hydroxyapatite 2 g | 0.56 mg | 10.3 mg | 0.44 g |
| 11 | cytochrome C 0.1 g | levanase 0.1 g | hydroxyapatite 2 g | 0.56 mg | 13.2 mg | 0.49 g |
| 12 | lysozyme 0.1 g | levanase 0.1 g | fluoroapatite 2 g | 2.24 mg | 13.7 mg | 0.45 g |
| 13 | lysozyme 0.1 g | levanase 0.1 g | hydroxyapatite 2 g | 4.48 mg | 15.3 mg | 0.32 g |
| 14 | lysozyme 0.1 g | mutanase 0.1 g | hydroxyapatite 2 g | 8.96 mg | 16.4 mg | 0.13 g |
| 15 | lysozyme 0.1 g | levanase 0.1 g | fluoroapatite 2 g | 18.0 mg | 19.0 mg | 0.04 g |

TABLE 1-continued

| NO. | Type & Amt. of Protein | Type & Amt. of Glucanase | Type & Amt. of Apatite | Glutaraldehyde | A | B |
|---|---|---|---|---|---|---|
| 16 | lysozyme 0.1 g | mutanase 0.1 g | hydroxyapatite 2 g | 18.0 mg | 17.4 mg | 0.02 g |
| 17 | lysozyme 0.2 g | dextranase 0.2 g | hydroxyapatite 5 g | 0 | 31.4 mg | 0.40 g |
| 18 | albumin 0.05 g | dextranase 0.05 g | hydroxyapatite 5 g | 1.0 mg | 10.9 mg | 0.51 g |
| 19 | lysozyme 0.05 g | dextranase 0.2 g | hydroxyapatite 5 g | 0.5 mg | 9.94 mg | 0.62 g |
| 20 | lysozyme 0.05 g | dextranase 0.2 g | hydroxyapatite 5 g | 10 mg | 15.2 mg | 0.46 g |
| 21 | lysozyme 0.025 g | dextranase 0.025 g | hydroxyapatite 2.5 g | 50 mg | 8.75 mg | 0.06 g |
| 22 | lysozyme 0.0125 g | dextranase 0.0125 g | hydroxyapatite 2.5 g | 50 mg | 12.37 mg | 0 |
| 23 | lysozyme 0.05 g | dextranase 0.05 g | fluoroapatite 5 g | 0.5 mg | 10.5 mg | 0.50 g |
| 24 | cytochrome C 0.05 g | dextranase 0.05 g | hydroxyapatite 5 g | 0.135 mg | 12.16 mg | 0.46 g |
| 25 | lysozyme 0.05 g | dextranase 0.05 g | fluoroapatite 5 g | 1.0 mg | 12.3 mg | 0.53 g |

A: total bonded protein/grams of apatite; B: amount of substrate decomposition/grams of protein

TABLE 2

Immobilizing Force of Hydroxyapatite to Dextronase

| Carrier | Eluting Concentration |
|---|---|
| Control | 0.08 mol |
| Lysozyme | 0.18 mol |
| Albumin | 0.12 mol |
| Casein | 0.15 mol |

TABLE 3

| | Change in enzymatic Activity of Immobilized Apatite with Time (specific activity) | | | | |
|---|---|---|---|---|---|
| No. | Just after Preparation | 4° C. 20 days | 4° C. 60 days | 36° C. 20 days | 36° C. 60 days |
| 1 | 100 | 213.6 | 98.0 | 154.0 | 70.5 |
| 2 | 100 | 303.3 | 110.4 | 136.7 | 57.2 |
| 3 | 100 | 278.8 | 121.9 | 150.6 | 68.4 |
| 4 | 100 | 241.6 | 95.8 | 155.0 | 70.5 |
| 5 | 100 | 293.0 | 112.9 | 327.0 | 126.8 |
| 6 | 100 | 287.4 | 108.7 | 320.4 | 120.8 |
| A | 100 | — | — | 68.4 | 27.3 |
| B | 100 | — | — | 65.3 | 25.8 |
| C | 100 | — | — | 58.7 | 20.3 |

A: Levanase only; B: Mutanase only; C: Dextranase only; each preserved in the form of an aqueous solution

What is claimed is:

1. A method for preparing an apatite having glucanase immobilized therein, comprising adding dropwise glutaraldehyde to an aqueous solution in which glucanase, lysozyme and apatite are present in a mixed state and recovering an apatite having glucanase immobilized therein.

2. The method according to claim 1, wherein the aqueous solution used is a buffer solution having a pH value ranging from 5.6 to 9.0.

3. The method according to claim 1, wherein the amount of glutaraldehyde is 0.3 to 6% relative to the amount of lysozyme 4. The method according to claim 1, wherein the apatite has a particle size of 2 to 200 microns.

5. The method of claim 1, wherein the glucanase is levanase.

6. The method of claim 1, wherein the glucanase is dextranase.

7. The method of claim 1, wherein the glucanase is mutanase.

8. The method of claim 1, wherein the apatite is hydroxyapatite.

9. The method of claim 1, wherein the apatite is fluroapatite.

10. A method of preparing an apatite with glucanase immobilized therein, comprising mixing a buffered aqueous solution having a pH ranging from 5.6 to 9.0 containing glucanase and lysozyme in equivalent amounts and apatite, said apatite having a particle size of 2 to 200 microns in an amount of 10 to 100 times as large as the amount of lysozyme, while adding glutaraldehyde dropwise thereto in an amount of 0.3% to 6% relative to the amount of lysozyme, and recovering an apatite having glucanase immobilized therein.

* * * * *